United States Patent
Shirota et al.

(10) Patent No.: US 11,116,460 B2
(45) Date of Patent: Sep. 14, 2021

(54) X-RAY IMAGING APPARATUS

(71) Applicant: Shimadzu Corporation, Kyoto (JP)

(72) Inventors: Ken Shirota, Kyoto (JP); Junpei Sakaguchi, Kyoto (JP); Hiroshi Okumura, Kyoto (JP)

(73) Assignee: Shimadzu Corporation, Kyoto (JP)

(*) Notice: Subject to any disclaimer, the term of this patent is extended or adjusted under 35 U.S.C. 154(b) by 56 days.

(21) Appl. No.: 16/597,864

(22) Filed: Oct. 10, 2019

(65) Prior Publication Data
US 2020/0205759 A1    Jul. 2, 2020

(30) Foreign Application Priority Data

Dec. 26, 2018 (JP) .............................. JP2018-242091

(51) Int. Cl.
*A61B 6/00* (2006.01)
*A61B 6/08* (2006.01)

(52) U.S. Cl.
CPC .............. *A61B 6/4482* (2013.01); *A61B 6/08* (2013.01); *A61B 6/4452* (2013.01); *A61B 6/54* (2013.01)

(58) Field of Classification Search
CPC ....... A61B 6/4482; A61B 6/08; A61B 6/4452; A61B 6/54; A61B 6/588; A61B 6/587; A61B 6/4464; A61B 6/4476; A61B 6/0487; A61B 6/40; A61B 6/44
See application file for complete search history.

(56) References Cited

U.S. PATENT DOCUMENTS

| | | | |
|---|---|---|---|
| 2007/0078534 A1* | 4/2007 | Boomgaarden | A61B 6/4429 700/63 |
| 2010/0213383 A1* | 8/2010 | Horiuchi | A61B 6/4482 250/393 |

FOREIGN PATENT DOCUMENTS

JP    2010-227376 A    10/2010

OTHER PUBLICATIONS

Product information from Canon Medical Systems Corporation, submitted with a partial English translation inserted into document (highlighted on first page), (this version or similar version available at least by Sep. 21, 2018). Available at https://jp.medical.canon/products/xray/radrex_drite.

* cited by examiner

*Primary Examiner* — Courtney D Thomas
(74) *Attorney, Agent, or Firm* — Muir Patent Law, PLLC (57) ABSTRACT

An X-ray imaging apparatus includes a controller configured or programmed to perform control to change an amount of assist from a drive in manually moving a moving body based on at least one of operation of an operation button configured to receive an operation for moving the moving body or an operation for aligning the moving body and a current position and target position of the moving body.

11 Claims, 3 Drawing Sheets

X-RAY IMAGING APPARATUS

CROSS-REFERENCE TO RELATED APPLICATIONS

This application claims the benefit of priority to Japanese Patent Application No. 2018-242091 filed on Dec. 26, 2018. The entire contents of this application are hereby incorporated herein by reference.

BACKGROUND OF THE INVENTION

Field of the Invention

The present invention relates to an X-ray imaging apparatus.

Description of the Background Art

Conventionally, an X-ray imaging apparatus is known. Such an X-ray imaging apparatus is disclosed in Japanese Patent Laid-Open No. 2010-227376, for example.

Japanese Patent Laid-Open No. 2010-227376 discloses a radiographic imaging apparatus (X-ray imaging apparatus) including a radiation source that irradiates a subject with X-rays, radiation detection means that detects the X-rays transmitted through the subject, a motor that moves the radiation source, and a control unit that assists in moving the radiation source by driving the motor when the radiation source is manually moved. In the radiographic imaging apparatus disclosed in Japanese Patent Laid-Open No. 2010-227376, when the radiation source is manually moved, the amount of assist from the motor is decreased when the moving direction of the radiation source is repeatedly reversed. That is, when the radiation source is manually moved, the amount of assist is increased in order to move the radiation source significantly and quickly at the beginning of movement, and the amount of assist is decreased in order to finely adjust the position when the radiation source gets close to a target position. At this time, the control unit determines that the radiation source has gotten close to the target position based on the repeated reversal of the moving direction of the radiation source.

However, in the radiographic imaging apparatus (X-ray imaging apparatus) disclosed in Japanese Patent Laid-Open No. 2010-227376, when the radiation source is manually moved, it is necessary to reciprocate the radiation source by repeatedly reversing the moving direction of the radiation source when it is attempted to decrease the amount of assist from the motor in order to finely adjust the position. Therefore, the operation becomes complicated when the amount of assist from the motor is changed.

SUMMARY OF THE INVENTION

The present invention is intended to solve the above problem. The present invention aims to provide an X-ray imaging apparatus in which the amount of assist from a drive can be changed by a simple operation when a moving body configured to movably support at least one of an X-ray irradiator and an X-ray detector is manually moved.

In order to attain the aforementioned object, an X-ray imaging apparatus according to an aspect of the present invention includes an X-ray irradiator configured to irradiate a subject with X-rays, an X-ray detector configured to detect the X-rays transmitted through the subject, a moving body configured to movably support at least one of the X-ray irradiator and the X-ray detector, a drive configured to move the moving body, and a controller configured or programmed to perform control to change an amount of assist from the drive in manually moving the moving body based on at least one of operation of an operation button configured to receive an operation for moving the moving body or an operation for aligning the moving body and a current position and target position of the moving body.

As described above, the X-ray imaging apparatus according to this aspect of the present invention includes the controller configured or programmed to perform control to change the amount of assist from the drive in manually moving the moving body based on at least one of the operation of the operation button configured to receive the operation for moving the moving body or the operation for aligning the moving body and the current position and target position of the moving body. Accordingly, when the amount of assist from the drive in manually moving the moving body is changed based on the operation of the operation button, the amount of assist from the drive can be changed simply by operating the operation button. When the amount of assist from the drive in manually moving the moving body is changed based on the current position and target position of the moving body, the amount of assist from the drive can be changed automatically when the target position gets close to the current position, for example. Consequently, when the moving body that movably supports at least one of the X-ray irradiator and the X-ray detector is manually moved, the amount of assist from the drive can be changed by a simple operation.

The aforementioned X-ray imaging apparatus according to this aspect preferably further includes a force detector configured to detect an operation force for moving the moving body, the operation force being applied by an operator, and the controller is preferably configured or programmed to perform control to adjust the amount of assist from the drive in manually moving the moving body in accordance with the operation force detected by the force detector, and also adjust the amount of assist based on at least one of the operation of the operation button and the current position and target position of the moving body. Accordingly, the amount of assist is adjusted in accordance with the detected operation force such that the amount of assist can be increased in accordance with the amount of force applied by the operator, and thus the operability at the time of manually moving the moving body can be improved. Furthermore, the amount of assist is adjusted based on the operation of the operation button such that the amount of assist can be easily changed simply by operating the operation button. In addition, the amount of assist is adjusted based on the current position and target position of the moving body such that the amount of assist can be increased when a distance between the current position and the target position is large and the moving body is to be moved quickly, and the amount of assist can be decreased when the distance between the current position and the target position is small and the moving body is to be moved accurately.

In the aforementioned X-ray imaging apparatus according to this aspect, the moving body is preferably configured to be movable along two axes in a horizontal direction and one axis in a vertical direction, the operation button preferably includes a first operation button and a second operation button, both of which are configured to receive the operation for moving the moving body, the first operation button is preferably configured to receive an operation for unlocking movement of the moving body along any one of the two axes in the horizontal direction and the one axis in the vertical direction, the second operation button is preferably configured to receive an operation for unlocking the movement of the moving body along two or more of the two axes in the horizontal direction and the one axis in the vertical direction, and the controller is preferably configured or programmed to perform control to further increase the amount of assist from the drive in manually moving the moving body when the second operation button is operated to unlock the movement of the moving body along the two or more axes than when the first operation button is operated to unlock the movement of the moving body along the any one axis. Accordingly, when the second operation button is operated to unlock the movement along the two or more axes and the moving body is to be moved significantly, the amount of assist can be increased. In addition, when the first operation button is operated to unlock the movement along the any one axis and the position of the moving body is finely adjusted after the adjustment due to the movement along the two or more axes, the amount of assist can be decreased.

The aforementioned X-ray imaging apparatus according to this aspect preferably further includes a guide illuminator configured to illuminate a guide indicating an X-ray irradiation range of the X-ray irradiator, the operation button preferably includes a guide illuminator button configured to receive an operation for aligning the moving body and turn on illumination of the guide of the guide illuminator, and the controller is preferably configured or programmed to perform control to further decrease the amount of assist from the drive in manually moving the moving body when the guide illuminator button is operated to turn on the guide illuminator than when the guide illuminator is turned off. Accordingly, when the guide illuminator button is operated to turn on the guide illuminator and the position of the moving body is finely adjusted, the amount of assist can be decreased, and thus the moving body can be moved easily and accurately to make fine adjustments.

In the aforementioned structure in which the operation button includes the first operation button and the second operation button or in the aforementioned structure in which the operation button includes the guide illuminator button, the controller is preferably configured or programmed to perform control to change the amount of assist by switching an assist coefficient, which is a ratio of the amount of assist to an operation force, between two stages. Accordingly, the amount of assist can be changed based on the assist ratios of the two stages, and thus the processing load on the controller can be reduced as compared with the case in which the assist coefficient is switched between three or more stages.

In the aforementioned X-ray imaging apparatus according to this aspect, the controller is preferably configured or programmed to perform control to change the amount of assist from the drive in manually moving the moving body based on a distance from the current position of the moving body to the target position of the moving body. Accordingly, the amount of assist is changed based on the distance of the moving body to the target position such that the amount of assist can be increased when the distance between the current position and the target position is large and the moving body is to be moved quickly, and the amount of assist can be decreased when the distance between the current position and the target position is small and the moving body is to be moved accurately. Thus, the moving body can be smoothly moved to the target position.

In the aforementioned X-ray imaging apparatus according to this aspect, the controller is preferably configured or programmed to perform control to further decrease the amount of assist from the drive in manually moving the moving body when force is applied to the moving body in a direction away from the target position than when the force is applied to the moving body in a direction toward the target position. Accordingly, the moving body can be difficult to move in the direction away from the target position, and the moving body can be easy to move in the direction toward the target position. Thus, the moving body can be guided to the target position.

In the aforementioned X-ray imaging apparatus according to this aspect, the drive preferably includes a motor, and the controller is preferably configured or programmed to perform control to change the amount of assist from the drive by changing drive control of the motor in manually moving the moving body based on at least one of the operation of the operation button and the current position and target position of the moving body. Accordingly, the drive control of the motor is changed such that the amount of assist can be easily changed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

(Structure of X-Ray Imaging Apparatus)

The structure of an X-ray imaging apparatus 100 according to the embodiment of the present invention is now described with reference to FIGS. 1 to 5.

Figure 1:
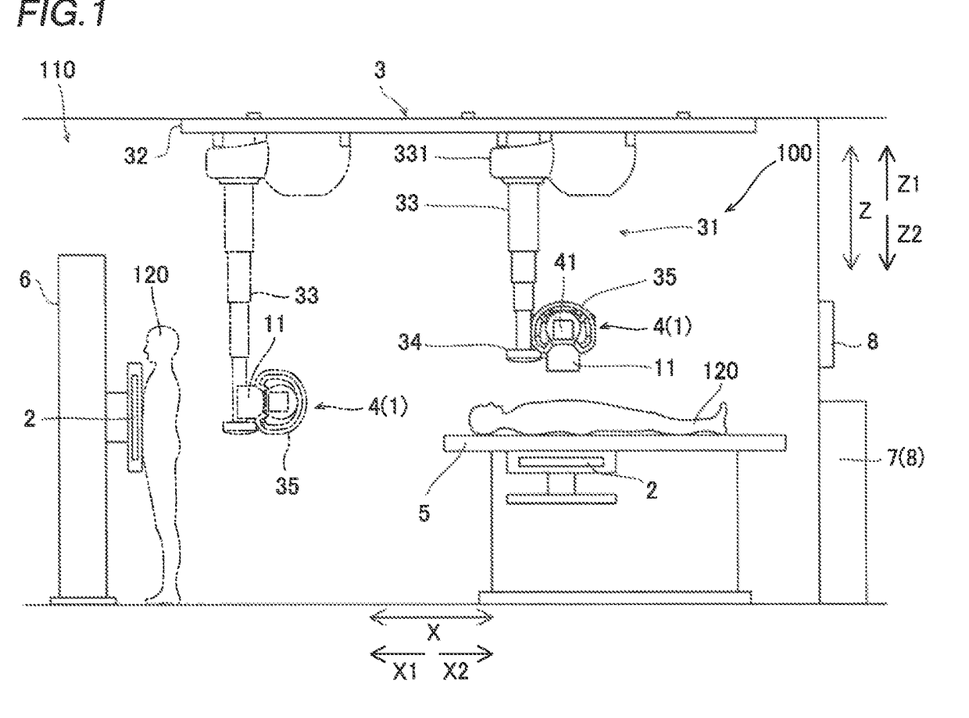
FIG. 1 is a schematic view showing the overall structure of an X-ray imaging apparatus according to an embodiment.

FIG. 1 shows an example of a ceiling-suspended X-ray imaging apparatus 100 installed in an imaging room 110. The X-ray imaging apparatus 100 includes an X-ray tube 1, X-ray detectors 2, and a holding mechanism 3. In the ceiling-suspended X-ray imaging apparatus 100, a moving body 4 including the X-ray tube 1 is held by the holding mechanism 3 disposed on the ceiling of the imaging room 110 so as to be suspended from the ceiling. The moving body 4 is held by the holding mechanism 3 in such a manner as to be movable in the imaging room 110. The X-ray tube 1 is an example of an "X-ray irradiator" in the claims.

The X-ray imaging apparatus 100 is a medical X-ray imaging apparatus, and is configured to radiograph a subject 120 (patient) to be imaged. The X-ray imaging apparatus 100 includes an imaging table 5 to image the lying subject 120 (in the recumbent position), and an imaging stand 6 to image the standing subject 120 (in the upright position).

The X-ray tube 1 is configured to irradiate the subject 120 with X-rays. The X-ray tube 1 is configured to radiate X-rays when a predetermined voltage is applied thereto.

The X-ray detectors 2 are movably held by the imaging table 5 and the imaging stand 6, respectively. The X-ray detectors 2 are flat panel detectors (FPDs), for example. The X-ray detectors 2 are configured to detect the X-rays transmitted through the subject 120. The holding mechanism 3 can move the moving body 4 at least between a position at which imaging in the recumbent position using the imaging table 5 is performed (see solid lines in FIG. 1) and a position at which imaging in the upright position using the imaging stand 6 is performed (see two-dot chain lines in FIG. 1).

In imaging in the recumbent position, the moving body 4 is disposed at a position that faces the X-ray detector 2 of the imaging table 5 in a vertical direction, and the subject 120 lying on the imaging table 5 is imaged between the X-ray tube 1 and the X-ray detector 2 that face each other in the vertical direction. In imaging in the upright position, the moving body 4 is disposed at a position that faces the X-ray detector 2 of the imaging stand 6 in a horizontal direction, and the subject 120 standing in front of the imaging stand 6 is imaged between the X-ray tube 1 and the X-ray detector 2 that face each other in the horizontal direction. Furthermore, in the X-ray imaging apparatus 100, a portable X-ray detector 2 is disposed at an arbitrary position in the imaging room 110, and the moving body 4 is moved to a position that faces the X-ray detector 2 such that general imaging (imaging in which the posture is not specified) in which the subject 120 in an arbitrary posture can be imaged from an arbitrary direction.

Figure 2:
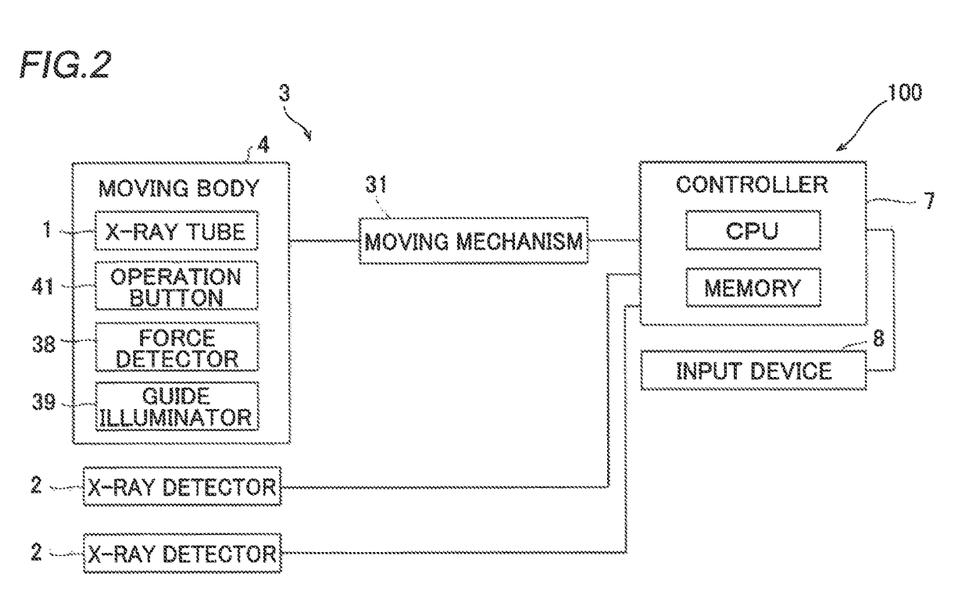
FIG. 2 is a block diagram of the X-ray imaging apparatus according to the embodiment.

The X-ray imaging apparatus 100 also includes a controller 7 and an input device 8. As shown in FIG. 2, the controller 7 includes a central processing unit (CPU) and a memory. The controller 7 controls X-ray imaging with the X-ray tube 1 and the X-ray detectors 2 and controls movement of the moving body 4. The input device 8 has a function of receiving an input operation related to X-ray imaging. The input operation includes setting of imaging conditions for X-ray imaging, an instruction to start X-ray irradiation, etc.

As shown in FIG. 1, the moving body 4 movably supports the X-ray tube 1. Specifically, the moving body 4 includes the X-ray tube 1 and a collimator 11. A high voltage is applied from a power supply (not shown) to the X-ray tube 1 such that the X-ray tube 1 generates X-rays. The collimator 11 includes a plurality of shielding plates (collimator leaves), the positions of which can be adjusted, and has a function of adjusting an X-ray field by partially shielding the X-rays from the X-ray tube 1. In addition, the moving body 4 is provided with a grip 35 (see FIG. 3). The moving body 4 includes operation buttons 41. The moving body 4 is also provided with a force detector 38 and a guide illuminator 39.

The holding mechanism 3 includes a moving mechanism 31 that holds the moving body 4 in such a manner that the moving body 4 is movable in a plurality of directions.

Figure 4:
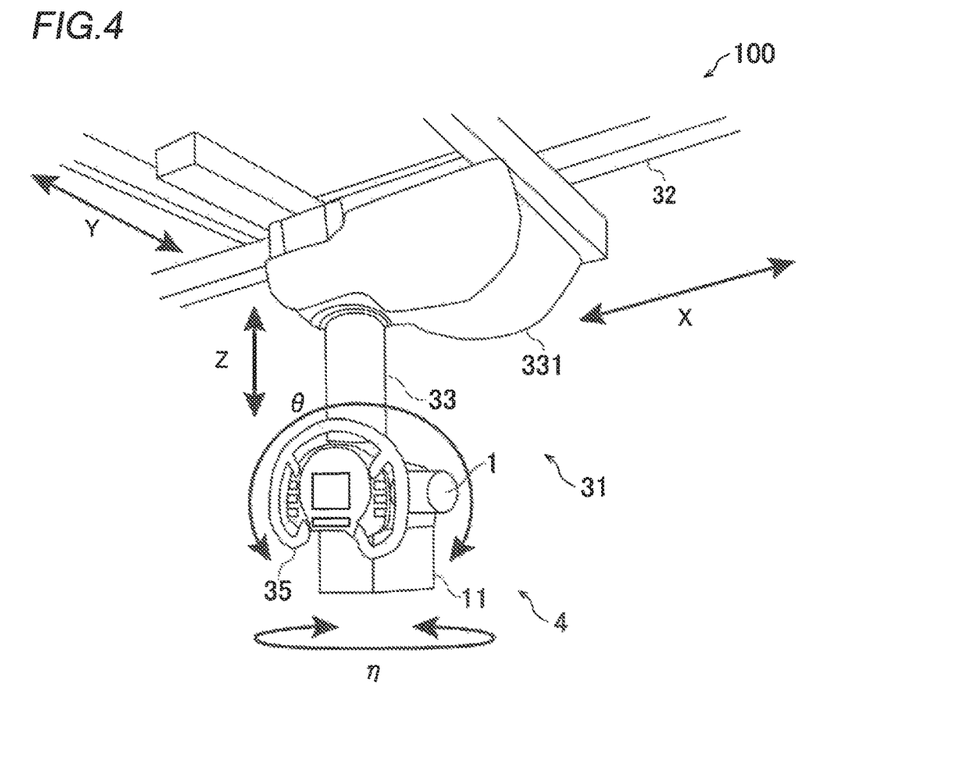
FIG. 4 is a perspective view showing the moving body of the X-ray imaging apparatus according to the embodiment.

The plurality of directions in which the moving mechanism 31 can move the moving body 4 can include horizontal and vertical translational directions orthogonal to each other. Assuming that a vertical direction is a Z direction and two directions orthogonal to each other in the horizontal direction are an X direction and a Y direction, as shown in FIG. 4, the translational direction(s) refers to one or a plurality of these X, Y, and Z directions. That is, the moving body 4 is configured to be movable along two axes in the horizontal direction and one axis in the vertical direction.

The plurality of directions in which the moving mechanism 31 can move the moving body 4 can include rotational directions about horizontal axes and a vertical axis orthogonal to each other. The rotational direction(s) refers to one or a plurality of the rotational direction about the vertical axis and the rotational directions about two axes orthogonal to each other in the horizontal direction. The plurality of directions are five directions in total including three translational directions (X, Y, and Z directions), a rotational direction ($\eta$ direction) about a rotation axis in the vertical direction (Z direction), and a rotational direction ($\theta$ direction) about a rotation axis in the horizontal direction.

As shown in FIG. 1, the moving mechanism 31 includes a traveling mechanism 32, a support rod 33, and a rotary holder 34. The traveling mechanism 32 is provided on the ceiling of the imaging room 110. The traveling mechanism 32 supports the support rod 33 in such a manner that the support rod 33 (moving body 4) can translate in the X direction and the Y direction.

The support rod 33 holds the moving body 4 in such a manner that the moving body 4 can translate in the vertical direction. The support rod 33 is suspended from a base 331 attached to the traveling mechanism 32, and is extendable in the Z direction. With these structures, the moving mechanism 31 holds the moving body 4 in such a manner that the moving body 4 is movable in the three translational directions (X, Y, and Z directions).

The rotary holder 34 is provided at the tip (lower end) of the support rod 33. The support rod 33 supports the rotary holder 34 in such a manner that the rotary holder 34 is rotatable in the $\eta$ direction about the vertical axis (Z-axis). The Z-axis coincides with the central axis of the support rod 33. The rotary holder 34 has a shape in which one end side is connected to the support rod 33 and another end side rises upward at a position offset in the radial direction (R-axis direction) of the support rod 33. The rotary holder 34 supports the moving body 4 at the position at which the rotary holder 34 rises upward.

The rotary holder 34 holds the moving body 4 in such a manner that the moving body 4 is rotatable in the $\theta$ direction about a horizontal axis (R-axis). The R-axis is in the radial direction (horizontal direction) of the support rod 33. With these structures, the moving mechanism 31 holds the moving body 4 in such a manner that the moving body 4 is movable in the two rotational directions ($\eta$ and $\theta$ directions).

The moving mechanism 31 includes the grip 35. The grip 35 is provided on the moving body 4, and is supported by the rotary holder 34 in such a manner as to rotate integrally with the moving body 4. The grip 35 is also supported by the support rod 33 in such a manner as to move integrally with the moving body 4. That is, the grip 35 is held by the support rod 33 via the rotary holder 34, and moves integrally with the moving body 4 in the plurality of directions (X, Y, Z, $\eta$, and $\theta$ directions). An operator can move the moving body 4 in the plurality of directions (X, Y, Z, $\eta$, and $\theta$ directions) by holding the grip 35 and applying force.

Figure 5:
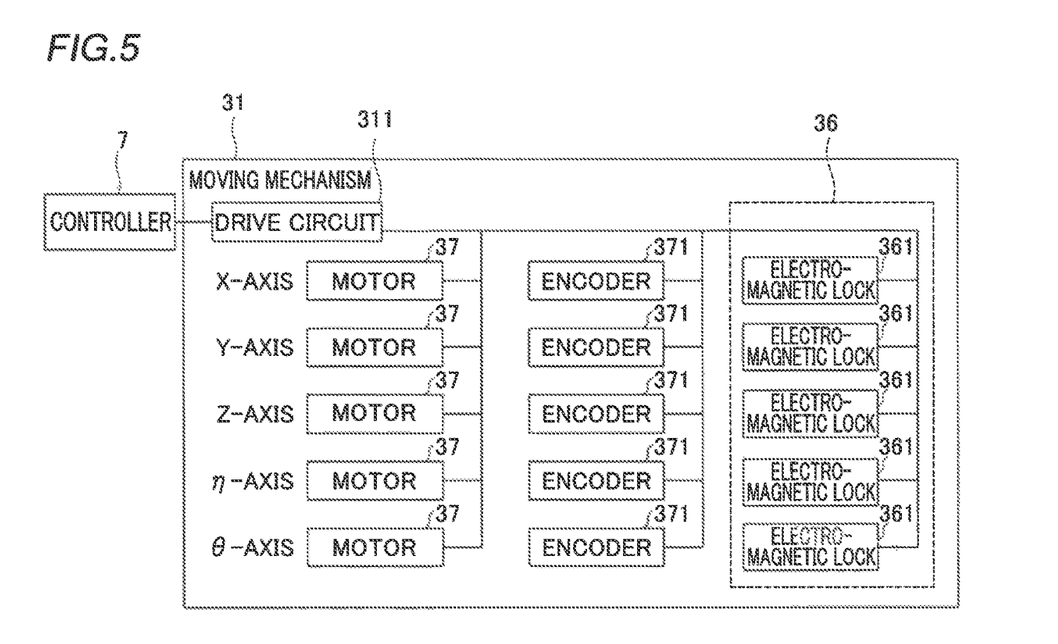
FIG. 5 is a block diagram showing an example of switching means of the X-ray imaging apparatus according to the embodiment.

The holding mechanism 3 includes the force detector 38 that detects an operation force for moving the moving body 4 applied by the operator. As shown in FIG. 5, the holding mechanism 3 includes a locking mechanism 36 that restricts movement of the moving body 4 in each of the plurality of directions (X, Y, Z, $\eta$, and $\theta$ directions), and motors 37 that respectively move the moving body 4 in the plurality of directions (X, Y, Z, $\eta$, and $\theta$ directions). The holding mechanism 3 includes encoders 371 that respectively detect the amount of movement of the moving body 4 in the plurality of directions (X, Y, Z, $\eta$, and $\theta$ directions). The motors 37 are examples of a "drive" in the claims.

As shown in FIG. 5, the locking mechanism 36 includes a plurality of electromagnetic locks 361 respectively corresponding to the plurality of directions and configured to lock movement of the moving body 4. The electromagnetic locks 361 releasably lock movement of the moving body 4 in the plurality of directions, respectively.

The electromagnetic locks 361 are individually provided in the plurality of directions, i.e. X, Y, Z, η, and θ directions. The electromagnetic locks 361 can individually switch between locking and unlocking in the X, Y, Z, η, and θ directions, respectively. Thus, the locking mechanism 36 can switch between a state of permitting movement of the moving body 4 in each of the plurality of directions (unlocking state) and a state of prohibiting movement of the moving body 4 in each of the plurality of directions (locking state).

The motors 37 are individually provided in the plurality of directions, i.e. X, Y, Z, η, and θ directions. The encoders 371 are individually provided in the plurality of directions, i.e. X, Y, Z, η, and θ directions. Each encoder 371 detects the position of the moving body 4 in each axial direction. Based on output signals from the encoders 371, the current position (the positions in the X, Y, and Z directions and the rotation angles in the η and θ directions) of the X-ray tube 1 of the moving body 4 can be obtained.

The operation of the locking mechanism 36 is controlled by the controller 7 via a drive circuit 311. Furthermore, the output signals from the encoders 37 are transmitted to the controller 7 via the drive circuit 311, and are used as operation information for operation control. The operation of each of the motors 37 is controlled by the controller 7 via the drive circuit 311.

The force detector 38 (see FIG. 2) detects the direction of force applied to the moving body 4. Specifically, the force detector 38 is configured to detect a force in each of the horizontal and vertical translational directions (X, Y, and Z directions) applied to the grip 35. In addition, the force detector 38 is configured to detect a force in each of the rotational directions (θ and η directions) about the horizontal axis (R-axis) and the vertical axis (Z-axis) applied to the grip 35.

More specifically, the force detector 38 is disposed between the grip 35 and the rotary holder 34. The force detector 38 includes a force sensor, for example. The force detector 38 is connected to the controller 7, and the operation force detected by the force detector 38 is converted into a signal and transmitted to the controller 7.

The guide illuminator 39 illuminates a guide indicating an X-ray irradiation range of the X-ray tube 1. Specifically, the guide illuminator 39 is configured to project the X-ray irradiation range of the X-ray tube 1 restricted by the collimator 11 with light. The guide illuminator 39 includes a light emitting diode (LED). The operator adjusts the position of the moving body 4 based on the guide of the guide illuminator 39 to adjust the X-ray irradiation position. Furthermore, the operator adjusts the collimator 11 based on the guide of the guide illuminator 39 to adjust the X-ray irradiation range.

Figure 3:
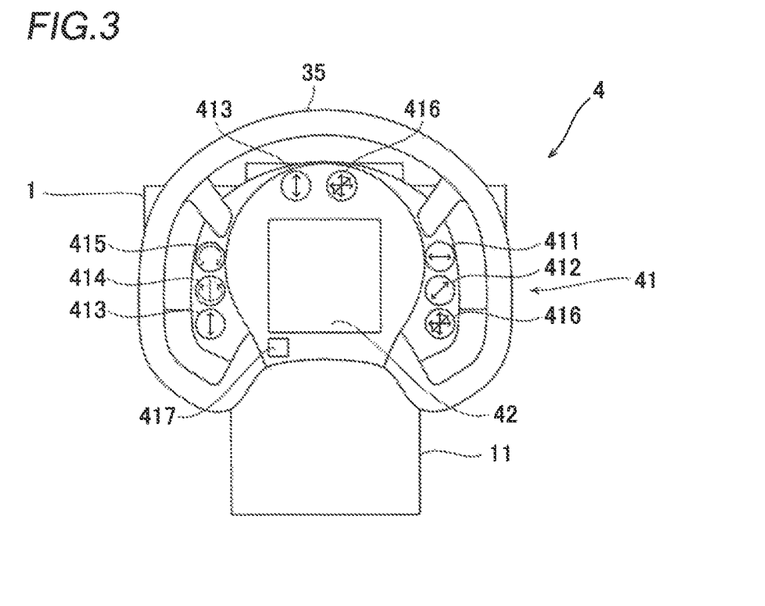
FIG. 3 is a front view of a moving body of the X-ray imaging apparatus according to the embodiment.

As shown in FIG. 3, the moving body 4 includes a plurality of operation buttons 41. The moving body 4 also includes a display 42. The operation buttons 41 include first operation buttons 411, 412, and 413 and a second operation button 416. The operation buttons 41 also include rotation operation buttons 414 and 415. The operation buttons 41 include a guide illuminator button 417.

The operation buttons 41 are configured to receive operations for moving the moving body 4. Each of the first operation buttons 411, 412, and 413 receives an operation for unlocking the movement along any one of the two axes in the horizontal direction and one axis in the vertical direction. The first operation button 411 receives an operation for unlocking movement of the moving body 4 in the X direction in the horizontal direction. The first operation button 412 receives an operation for unlocking movement of the moving body 4 in the Y direction in the horizontal direction. The first operation button 413 receives an operation for unlocking movement of the moving body 4 in the vertical direction (Z direction). The second operation button 416 receives an operation for unlocking the movement along two or more of the two axes in the horizontal direction and one axis in the vertical direction. Specifically, the second operation button 416 receives an operation for unlocking the movement in the X direction, the Y direction, and the Z direction.

The guide illuminator button 417 receives an operation for aligning the moving body 4. Specifically, the guide illuminator button 417 receives an operation for turning on illumination of the guide of the guide illuminator 39.

The controller 7 is configured or programmed to control movement of the moving body 4. Specifically, the controller 7 is configured or programmed to control the moving body 4 to move to a predetermined position and pose in automatic positioning control. The controller 7 is configured or programmed to perform control to power-assist in moving the moving body 4 in power assist control when the operator manually moves the moving body 4.

In the power assist control, the controller 7 controls the force detector 38 to detect the operation force for manually moving the moving body 4 applied by the operator, and acquires the operation force. Then, the controller 7 corrects the influence of the weight and pose of the moving body 4 to convert the acquired operation force into operation forces in the X direction, the Y direction, and the Z direction. Then, the controller 7 controls the motors 37 to be driven such that torques obtained by multiplying the converted operation forces by an assist ratio are generated. For example, the controller 7 performs control to drive the motor(s) 37 with an amount of assist of $\alpha f_h$ based on an equation (1):

$$Ma = f_h - F_r + \alpha f_h \qquad (1)$$

where M represents the mass of a moving portion including the moving body 4 and the moving mechanism 31, a represents an acceleration, $f_h$ represents an operation force, $F_r$ represents a resistance force, and a represents an assist coefficient, which is a ratio of the amount of assist to the operation force. M is several hundred kg, for example. In addition, a is about 2 to 10, for example. That is, the operator's operation is assisted by a force of two to ten times the operation force.

In this embodiment, the controller 7 is configured or programmed to perform control to change the amount of assist from the motors 37 in manually moving the moving body 4 based on at least one of the operation of the operation buttons 41 that receive operations for moving the moving body 4 or an operation for aligning the moving body 4 and the current position and target position of the moving body 4. Specifically, the controller 7 is configured or programmed to perform control to adjust the amount of assist from the motors 37 in manually moving the moving body 4 in accordance with the operation force detected by the force detector 38, and also adjust the amount of assist based on at least one of the operation of the operation buttons 41 and the current position and target position of the moving body 4.

That is, the controller 7 is configured or programmed to increase the amount of assist from the motors 37 in manually moving the moving body 4 when it is attempted to significantly move the moving body 4. Furthermore, the controller 7 is configured or programmed to decrease the amount of assist from the motors 37 in manually moving the moving body 4 when it is attempted to accurately move the moving body 4.

The controller 7 is configured or programmed to perform control to further increase the amount of assist from the motors 37 in manually moving the moving body 4 when the second operation button 416 is operated to unlock the movement along two or more axes than when the first operation button 411, 412, or 413 is operated to unlock the movement along any one axis. That is, the controller 7 is configured or programmed to change the amount of assist depending on the operated operation button 41. Generally, the operation of significantly moving the moving body 4 is required when switching between imaging in the upright position and imaging in the recumbent position is performed. In this case, first, the second operation button 416 is operated to unlock the movement along three axes simultaneously and move the moving body 4 near the predetermined position. Thereafter, the first operation button 411, 412, or 413 is operated to unlock the movement along only one axis and precisely align the moving body 4 with the predetermined position. Therefore, the controller 7 increases the amount of assist when the second operation button 416 is operated to unlock the movement along the three axes simultaneously. Furthermore, the controller 7 decreases the amount of assist when the first operation button 411, 412, or 413 is operated to unlock the movement along only one axis. Thus, it is possible to achieve both the operation of significantly moving the moving body 4 and the operation of finely moving the moving body 4. In addition, a common imaging apparatus has various uses such as imaging on a stretcher, and thus it is also contemplated that it may be desired to significantly move the moving body 4 while moving the moving body 4 along only one axis. When it is possible to provide a plurality of buttons to unlock the movement along a certain axis, one button may be operated to increase the amount of assist, and the other button may be operated to decrease the amount of assist.

The controller 7 is configured or programmed to perform control to further decrease the amount of assist from the motors 37 in manually moving the moving body 4 when the guide illuminator button 417 is operated to turn on the guide illuminator 39 than when the guide illuminator 39 is turned off. That is, when the moving body 4 gets close to the predetermined position and is precisely aligned with a region to be imaged, the guide illuminator 39 (collimator lamp) is turned on to confirm the X-ray irradiation field. Therefore, the controller 7 determines that the position of the X-ray tube 1 is to be finely adjusted when the operation of turning on the guide illuminator 39 is performed, and decreases the amount of assist.

The controller 7 is configured or programmed to perform control to change the amount of assist by switching the assist coefficient, which is the ratio of the amount of assist to the operation force, between two stages. That is, the controller 7 sets the assist coefficient to a small value when decreasing the amount of assist, and sets the assist coefficient to a large value when increasing the amount of assist. For example, the value of the large assist coefficient is set to about two to three times the value of the small assist coefficient.

The controller 7 is configured or programmed to perform control to change the amount of assist from the motors 37 in manually moving the moving body 4 based on a distance from the current position of the moving body 4 to the target position. Specifically, when switching between imaging in the upright position and imaging in the recumbent position is performed, the moving body 4 (X-ray tube 1) is moved to a position that faces the corresponding X-ray detector 2 after an imaging menu is selected in advance via the input device 8. At this time, the position of the X-ray tube 1 relative to the imaging table 5 or the imaging stand 6 can be detected by a potentiometer or an encoder in order to adjust the source-image distance (SID) of the X-ray tube 1 to the X-ray detector 2 or the height of the X-ray tube 1 relative to the X-ray detector 2. The controller 7 acquires the current position of the moving body 4 and acquires the distance between the X-ray detector 2 and the X-ray tube 1 used in the selected imaging menu. Then, the controller 7 changes the amount of assist in accordance with the distance from the current position of the moving body 4 to the target position. That is, the controller 7 increases the amount of assist when the distance is large, and decreases the amount of assist when the distance is small. Note that the magnitude of the distance may be determined based on a threshold, and the amount of assist may be changed based on the threshold. Alternatively, the amount of assist may be gradually decreased as the distance gets smaller. Alternatively, the amount of assist may be constant up to a certain distance, and the amount of assist may be gradually decreased as the distance gets smaller than the certain distance. Alternatively, the amount of assist may be decreased in a stepwise fashion in accordance with the distance.

The controller 7 is configured or programmed to perform control to further decrease the amount of assist from the motors 37 in manually moving the moving body 4 when force is applied to the moving body 4 in a direction away from the target position than when force is applied to the moving body 4 in a direction toward the target position. Thus, it is possible to obtain the operation feeling like being sucked into the target position.

Advantages of this Embodiment

According to this embodiment, the following advantages are obtained.

According to this embodiment, as described above, the X-ray imaging apparatus 100 includes the controller 7 configured or programmed to perform control to change the amount of assist from the motors 3 in manually moving the moving body 4 based on at least one of the operation of the operation buttons 41 configured to receive the operations for moving the moving body 4 or the operation for aligning the moving body 4 and the current position and target position of the moving body 4. Accordingly, when the amount of assist from the motors 37 in manually moving the moving body 4 is changed based on the operation of the operation buttons 41, the amount of assist from the motors 37 can be changed simply by operating the operation buttons 41. When the amount of assist from the motors 37 in manually moving the moving body 4 is changed based on the current position and target position of the moving body 4, the amount of assist from the motors 37 can be changed automatically when the target position gets close to the current position. Consequently, when the moving body 4 that movably supports the X-ray tube 1 is manually moved, the amount of assist from the motors 37 can be changed by a simple operation.

According to this embodiment, as described above, the controller 7 is configured or programmed to perform control to adjust the amount of assist from the motors 37 in manually moving the moving body 4 in accordance with the operation force detected by the force detector 38, and also adjust the amount of assist based on at least one of the operation of the operation buttons 41 and the current position and target position of the moving body 4. Accordingly, the amount of assist is adjusted in accordance with the detected operation force such that the amount of assist can be increased in accordance with the amount of force applied by the operator, and thus the operability at the time of manually moving the moving body 4 can be improved. Furthermore, the amount of assist is adjusted based on the operation of the operation buttons 41 such that the amount of assist can be easily changed simply by operating the operation buttons 41. In addition, the amount of assist is adjusted based on the current position and target position of the moving body 4 such that the amount of assist can be increased when the distance between the current position and the target position is large and the moving body 4 is to be moved quickly, and the amount of assist can be decreased when the distance between the current position and the target position is small and the moving body 4 is to be moved accurately.

According to this embodiment, as described above, the controller 7 is configured or programmed to perform control to further increase the amount of assist from the motors 37 in manually moving the moving body 4 when the second operation button 416 is operated to unlock the movement along the two or more axes than when the first operation button 411, 412, or 413 is operated to unlock the movement along any one axis. Accordingly, when the second operation button 416 is operated to unlock the movement along the two or more axes and the moving body 4 is to be moved significantly, the amount of assist can be increased. In addition, when the first operation button 411, 412, or 413 is operated to unlock the movement along any one axis and the position of the moving body 4 is finely adjusted after the adjustment due to the movement along the two or more axes, the amount of assist can be decreased.

According to this embodiment, as described above, the controller 7 is configured or programmed to perform control to further decrease the amount of assist from the motors 37 in manually moving the moving body 4 when the guide illuminator button 417 is operated to turn on the guide illuminator 39 than when the guide illuminator 39 is turned off. Accordingly, when the guide illuminator button 417 is operated to turn on the guide illuminator 39 and the position of the moving body 4 is finely adjusted, the amount of assist can be decreased, and thus the moving body 4 can be moved easily and accurately to make fine adjustments.

According to this embodiment, as described above, the controller 7 is configured or programmed to perform control to change the amount of assist by switching the assist coefficient, which is the ratio of the amount of assist to the operation force, between the two stages. Accordingly, the amount of assist can be changed based on the assist ratios of the two stages, and thus the processing load on the controller 7 can be reduced as compared with the case in which the assist coefficient is switched between three or more stages.

According to this embodiment, as described above, the controller 7 is configured or programmed to perform control to change the amount of assist from the motors 37 in manually moving the moving body 4 based on the distance from the current position of the moving body 4 to the target position. Accordingly, the amount of assist is changed based on the distance of the moving body 4 to the target position such that the amount of assist can be increased when the distance between the current position and the target position is large and the moving body 4 is to be moved quickly, and the amount of assist can be decreased when the distance between the current position and the target position is small and the moving body 4 is to be moved accurately. Thus, the moving body 4 can be smoothly moved to the target position.

According to this embodiment, as described above, the controller 7 is configured or programmed to perform control to further decrease the amount of assist from the motors 37 in manually moving the moving body 4 when force is applied to the moving body 4 in the direction away from the target position than when force is applied to the moving body 4 in the direction toward the target position. Accordingly, the moving body 4 can be difficult to move in the direction away from the target position, and the moving body 4 can be easy to move in the direction toward the target position. Thus, the moving body 4 can be guided to the target position.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the ceiling-suspended X-ray imaging apparatus (ceiling-suspended holding mechanism) is shown as an example in the aforementioned embodiment, the present invention is not limited to this. The present invention may alternatively be applied to a structure other than the ceiling-suspended structure. For example, the present invention may be applied to a floor traveling X-ray imaging apparatus. Alternatively, the present invention may be applied to a C-arm type X-ray imaging apparatus, or the present invention may be applied to a proximate fluoroscopic table. Alternatively, the present invention may be applied to a cart-type X-ray imaging apparatus including wheels.

While the moving body movably supports the X-ray tube (X-ray irradiator) in the aforementioned embodiment, the present invention is not limited to this. In the present invention, the moving body may alternatively movably support both the X-ray irradiator and the X-ray detector, or the moving body may alternatively movably support the X-ray detector.

While the moving mechanism holds the moving body in such a manner that the moving body is movable in the plurality of directions, i.e. the five axial directions (X direction, Y direction, Z direction, η direction, and θ direction), in the aforementioned embodiment, the present invention is not limited to this. In the present invention, the moving mechanism may alternatively hold the moving body in such a manner that the moving body is movable in a direction other than the five directions.

While the second operation button receives the operation for unlocking the movement along the three axes, i.e. the X-axis, the Y-axis, and the Z-axis, in the aforementioned embodiment, the present invention is not limited to this. In the present invention, the second operation button may alternatively receive an operation for unlocking the movement along two or more of the two axes in the horizontal direction and one axis in the vertical direction.

While the controller is disposed outside the imaging room in the aforementioned embodiment, the present invention is not limited to this. The controller may alternatively be disposed inside the imaging room, or may be built in the moving body or the moving mechanism.

What is claimed is:

1. An X-ray imaging apparatus comprising:
an X-ray irradiator configured to irradiate a subject with X-rays;
an X-ray detector configured to detect the X-rays transmitted through the subject;
a moving body configured to movably support at least one of the X-ray irradiator and the X-ray detector;
a drive configured to move the moving body; and
a controller configured or programmed to perform control to change an amount of assist from the drive in manually moving the moving body based on an operation of an operation button configured to receive an operation for moving the moving body,
wherein the controller is configured or programmed to change the amount of assist from the drive according to the number of axes on which the moving body moves based on the operation of the operation button.

2. The X-ray imaging apparatus according to claim 1, further comprising a force detector configured to detect an operation force for moving the moving body, the operation force being applied by an operator; wherein
the controller is configured or programmed to perform control to adjust the amount of assist from the drive in manually moving the moving body in accordance with the operation force detected by the force detector, and also adjust the amount of assist based on the operation of the operation button and the current position.

3. The X-ray imaging apparatus according to claim 1, wherein
the moving body is configured to be movable along two axes in a horizontal direction and one axis in a vertical direction;
the operation button includes a first operation button and a second operation button, both of which are configured to receive the operation for moving the moving body;
the first operation button is configured to receive an operation for unlocking movement of the moving body along any one of the two axes in the horizontal direction and the one axis in the vertical direction;
the second operation button is configured to receive an operation for unlocking the movement of the moving body along two or more of the two axes in the horizontal direction and the one axis in the vertical direction; and
the controller is configured or programmed to perform control to further increase the amount of assist from the drive in manually moving the moving body when the second operation button is operated to unlock the movement of the moving body along the two or more axes than when the first operation button is operated to unlock the movement of the moving body along the any one axis.

4. The X-ray imaging apparatus according to claim 1, wherein
the drive includes a motor; and
the controller is configured or programmed to perform control to change the amount of assist from the drive by changing drive control of the motor in manually moving the moving body based on the operation of the operation button.

5. The X-ray imaging apparatus according to claim 3, wherein the controller is configured or programmed to perform control to change the amount of assist by switching an assist coefficient, which is a ratio of the amount of assist to an operation force, between two stages.

6. An X-ray imaging apparatus comprising:
an X-ray irradiator configured to irradiate a subject with X-rays;
an X-ray detector configured to detect the X-rays transmitted through the subject;
a moving body configured to movably support at least one of the X-ray irradiator and the X-ray detector;
a drive configured to move the moving body; and
a controller configured or programmed to perform control to change an amount of assist from the drive in manually moving the moving body based on a current position and target position of the moving body.

7. The X-ray imaging apparatus according to claim 6, further comprising:
a force detector configured to detect an operation force for moving the moving body, the operation force being applied by an operator, wherein
the controller is configured or programmed to perform control to adjust the amount of assist from the drive in manually moving the moving body in accordance with the operation force detected by the force detector, and also adjust the amount of assist based on the current position and target position of the moving body.

8. The X-ray imaging apparatus according to claim 6, wherein the controller is configured or programmed to perform control to change the amount of assist from the drive in manually moving the moving body based on a distance from the current position of the moving body to the target position of the moving body.

9. The X-ray imaging apparatus according to claim 6, wherein the controller is configured or programmed to perform control to further decrease the amount of assist from the drive in manually moving the moving body when force is applied to the moving body in a direction away from the target position than when the force is applied to the moving body in a direction toward the target position.

10. The X-ray imaging apparatus according to claim 6, wherein
the drive includes a motor; and
the controller is configured or programmed to perform control to change the amount of assist from the drive by changing drive control of the motor in manually moving the moving body based on the current position and target position of the moving body.

11. An X-ray imaging apparatus comprising:
an X-ray irradiator configured to irradiate a subject with X-rays;
an X-ray detector configured to detect the X-rays transmitted through the subject;
a moving body configured to movably support at least one of the X-ray irradiator and the X-ray detector;
a drive configured to move the moving body;
a controller configured or programmed to perform control to change an amount of assist from the drive in manually moving the moving body based on at least one of operation of an operation button configured to receive an operation for moving the moving body or an operation for aligning the moving body and a current position and target position of the moving body; and
a guide illuminator configured to illuminate a guide indicating an X-ray irradiation range of the X-ray irradiator; wherein
the operation button includes a guide illuminator button configured to receive an operation for aligning the moving body and turn on illumination of the guide of the guide illuminator; and
the controller is configured or programmed to perform control to further decrease the amount of assist from the drive in manually moving the moving body when the guide illuminator button is operated to turn on the guide illuminator than when the guide illuminator is turned off.

* * * * *